US008410085B2

(12) United States Patent
Moore et al.

(10) Patent No.: US 8,410,085 B2
(45) Date of Patent: Apr. 2, 2013

(54) PHOSPHOLIPID COMPOSITIONS AND USES THEREOF

(75) Inventors: David D. Moore, Bellaire, TX (US); Jae Man Lee, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 288 days.

(21) Appl. No.: 12/742,879

(22) PCT Filed: Nov. 17, 2008

(86) PCT No.: PCT/US2008/012846
§ 371 (c)(1),
(2), (4) Date: Sep. 8, 2010

(87) PCT Pub. No.: WO2009/067182
PCT Pub. Date: May 28, 2009

(65) Prior Publication Data
US 2010/0331281 A1    Dec. 30, 2010

Related U.S. Application Data

(60) Provisional application No. 60/988,505, filed on Nov. 16, 2007.

(51) Int. Cl.
*A01N 43/00*   (2006.01)
*A01N 57/26*   (2006.01)
*A61K 31/33*   (2006.01)
*A61K 31/685*  (2006.01)

(52) U.S. Cl. .......................................... 514/183; 514/77
(58) Field of Classification Search .................... 514/77, 514/183
See application file for complete search history.

(56) References Cited

U.S. PATENT DOCUMENTS

| | | | |
|---|---|---|---|
| 2003/0040505 | A1 | 2/2003 | Fogelman et al. |
| 2004/0023922 | A1 | 2/2004 | Porter |
| 2005/0096307 | A1 | 5/2005 | Graziano |

FOREIGN PATENT DOCUMENTS

| | | |
|---|---|---|
| WO | WO 97/39759 | 10/1997 |
| WO | WO-2004/039430 A2 | 5/2004 |
| WO | WO-2004/108140 A1 | 12/2004 |
| WO | WO-2005/107711 A2 | 11/2005 |
| WO | WO-2007/065156 A2 | 6/2007 |

OTHER PUBLICATIONS

International Search Report for PCT/US2008/012846, mailed Jun. 10, 2009.
Coste et al., "LRH-1-mediated glucocorticoid synthesis in enterocytes protects against inflammatory bowel disease," *Proc. Natl. Acad. Sci. U.S.A.* 104: 13098-13103 (2007).
Dhe-Paganon et al., "Crystal structure of the HNF4α ligand binding domain in complex with endogenous fatty acid ligand," *J. Biol. Chem.* 277: 37973-37976 (2002).
Francis et al., "Nuclear receptors and the control of metabolism," *Annu. Rev. Physiol.* 65: 261-311 (2003).
Hunt, "Dynamic lipidomics of the nucleus," *J. Cell. Biochem.* 97: 244-251 (2006).
Krylova et al., "Structural analyses reveal phosphatidyl inositols as ligands for the NR5 orphan receptors SF-1 and LRH-1," *Cell* 120: 343-355 (2005).
Lee et al., "Role for peroxisome proliferator-activated receptor α in oxidized phospholipid-induced synthesis of monocyte chemotactic protein-1 and interleukin-8 by endothelial cells," *Circ. Res.* 87: 516-521 (2000).
Li et al., "Crystallographic identification and functional characterization of phospholipids as ligands for the orphan nuclear receptor steroidogenic factor-1," *Mol. Cell* 17: 491-502 (2005).
Li et al., "Cyclic AMP-stimulated interaction between steroidogenic factor 1 and diacylglycerol kinase θ facilitates induction of CYP17," *Mol. Cell. Biol.* 27: 6669-6685 (2007).
McIntyre et al., "Identification of an intracellular receptor for lysophosphatidic acid (LPA): LPA is a transcellular PPARγ agonist," *Proc. Natl. Acad. Sci. U.S.A.* 100: 131-136 (2003).
Ortlund et al., "Modulation of human nuclear receptor LRH-1 activity by phospholipids and SHP," *Nat. Struct. Mol. Biol.* 12: 357-363 (2005).
Sablin et al., "Structural basis for ligand-independent activation of the orphan nuclear receptor LRH-1," *Mol. Cell* 11: 1575-1585 (2003).
Tsukahara et al., "Different residues mediate recognition of 1-O-oleyllysophosphatidic acid and rosiglitazone in the ligand binding domain of peroxisome proliferator-activated receptor γ," *J. Biol. Chem.* 281: 3398-3407 (2006).
Urs et al., "Sphingosine regulates the transcription of CYP17 by binding to steroidogenic factor-1," *Endocrinology* 147: 5249-5258 (2006).
Wang et al., "The crystal structures of human steroidogenic factor-1 and liver receptor homologue-1," *Proc. Natl. Acad. Sci. U.S.A.* 102: 7505-7510 (2005).
Whitby et al., "Identification of small molecule agonists of the orphan nuclear receptors liver receptor homolog-1 and steroidogenic factor-1," *J. Med. Chem.* 49: 6652-6655 (2006).
Wisely et al., "Hepatocyte nuclear factor 4 is a transcription factor that constitutively binds fatty acids," *Structure* 10: 1225-1234 (2002).
Zhang et al., "Lysophosphatidic acid induces neointima formation through PPARγ activation," *J. Exp. Med.* 199: 763-774 (2004).
Extended European Search Report for International Application No. PCT/US2008/012846, dated Oct. 11, 2010 (10 pages).

*Primary Examiner* — Marcos Sznaidman
(74) *Attorney, Agent, or Firm* — Clark & Elbing LLP

(57) ABSTRACT

We have discovered that phospholipids diundecanoyl (C11:0-C11:0) and dilauroyl (C12:0-C12:0) phosphatidylcholine (PC) act as agonists of the LRH-1 receptor. We have also shown that administration of these lipids to diabetic mice reduces blood glucose levels. On the basis of these discoveries, the present invention features compositions that include these lipids and structurally related lipids. Also featured are methods of treating metabolic disorders and inflammatory bowel disease, lowering blood glucose levels, and increasing LRH-1 receptor activity in a subject by administration of these lipids.

6 Claims, 9 Drawing Sheets

A

B

C

US 8,410,085 B2

PHOSPHOLIPID COMPOSITIONS AND USES THEREOF

CROSS REFERENCE TO RELATED APPLICATIONS

This application is the U.S. National Stage of International Application PCT/US2008/012846, filed Nov. 17, 2008, which claims priority from U.S. Provisional Application No. 60/988,505, filed Nov. 16, 2007.

STATEMENT AS TO FEDERALLY FUNDED RESEARCH

This invention was made with United States Government support under grant RO1 DK068804 awarded by the National Institute of Diabetes and Digestive and Kidney Diseases at the National Institutes of Health. The Government has certain rights to this invention.

BACKGROUND OF THE INVENTION

The invention relates to lipid compositions and methods of using the lipid compositions for treatment of metabolic disorders, including diabetes and inflammatory bowel disease.

The orphan nuclear receptor LRH-1/NR5A2 is expressed in the liver, intestine, exocrine pancreas, and ovary. It binds DNA as a monomer and is best known as a regulator of hepatic expression of the key bile acid biosynthetic enzyme Cyp7A1 but is also reported to regulate expression of a number of other genes associated with bile acid and cholesterol homeostasis, as well as other metabolic targets. It is expressed in embryonic stem cells and initial stages of embryonic development. The very early lethality of LRH-1 null mice both highlights its essential developmental role and precludes straightforward knockout studies that have been so useful for delineating the functions of other orphan and former orphan receptors.

Analysis of LRH-1 function has also been hindered by the absence of appropriate agonist or antagonist ligands. A series of crystal structures of LRH-1 and its closest relative SF-1 (NR5A1) has recently identified phospholipids as potential ligands, but their function as modulators of receptor signaling has remained uncertain.

Thus, additional agonists for LRH-1 would be highly desirable.

SUMMARY OF THE INVENTION

We have discovered that the LRH-1 receptor is potently activated by phosphatidylcholine lipids having 22-24 total carbons in their fatty acid tails. Specifically, we have shown that diundecanoyl (C11:0-C11:0) and dilauroyl (C12:0-C12:0) phosphatidylcholine (PC), referred to as DUPC and DLPC, respectively are LRH-1 agonists. Surprisingly, other PC lipids having different chain lengths and lipids with other head groups did not activate this receptor. Importantly, we also have discovered that administration of DUPC and DLPC to diabetic mice improves insulin sensitivity. Administration to normal mice results in alteration of bile acid pools. Based on these results, and as described herein, we believe LRH-1 is a key metabolic regulator and that agonists such as DUPC and DLPC can have beneficial effects in treatment of metabolic disorders such as diabetes, as well other diseases linked to LRH-1 receptor activity, such as inflammatory bowel disease.

Accordingly, in a first aspect the invention features a composition including at least one (e.g., two, three, or four) phosphatidylcholine (PC) lipid(s) having 22, 23, or 24 total carbon atoms in its fatty acid tails (e.g., where the fatty acid tails each are 10, 11, 12, or 13 carbon atoms in length, such as the lipids described herein). Particular lipids include those selected from the group consisting of diundecanoylphosphatidylcholine (DUPC), dilauroylphosphatidylcholine (DLPC), a C11:0, C12:0 undecanoyl, lauroyl PC, a C11:0, C13:0 undecanoyl, tridecanoyl PC, and a C10:0, C12:0 decanoyl, lauroyl PC, or a combination thereof. The composition may be enriched. The lipid(s) may be present with a pharmaceutically acceptable carrier. The lipid(s) may be from about 0.01% to about 99% (e.g., from about 0.1% to about 50%) of the composition. The composition may contain at least 1, 5, 10, 25, 50, 100, 250, 500, or 750 µg; at least 1, 2, 5, 10, 25, 50, 100, 250, 500, or 750 mg; or at least 1, 2, 5, 10, 15, 20, 25, 50, 100, or 200 g of the lipid(s), or any range between these values. The composition may be in any pharmaceutically acceptable form described herein (e.g., a tablet or a liquid formulation). In certain embodiments, the composition is food supplemented with the lipid(s) (e.g., DUPC or DLPC). The lipid(s) may be present in the composition in an amount sufficient to treat a metabolic disorder (e.g., any described herein, such as diabetes) or inflammatory bowel disease. In certain embodiments, the lipid(s) are present in the composition in a non-liposomal form. In certain embodiments, the lipid(s) are formulated with bile acids (e.g., taurocholic acid, glycocholic acid, cholic acid, chenodeoxycholic acid, deoxycholic acid, or lithocholic acid).

In another aspect, the invention features a method of treating a subject (e.g., a human) having a metabolic disorder. The method includes administering an effective amount of a lipid or lipids of the first aspect (e.g., any composition described herein) to the subject. The metabolic disorder may be selected from the group consisting of type I diabetes, type II diabetes, maturity-onset diabetes of the young (MODY), gestational diabetes, obesity, satiety, and endocrine deficiencies of aging.

In another aspect, the invention features a method of treating a subject (e.g., a human) having inflammatory bowel disease. The method includes administering an effective amount of a lipid(s) of the first aspect (e.g., any composition described herein) to the subject.

In yet another aspect, the invention features a method of reducing blood glucose levels in a subject (e.g., a human). The method includes administering an effective amount of a lipid(s) of the first aspect (e.g., any composition described herein) to the subject. The subject may be hyperglycemic.

Further, the invention features a method of increasing LRH-1 receptor activity in a subject (e.g., a human), the method including administering to the subject an effective amount of a lipid(s) of the first aspect (e.g., any composition described herein).

In any of the methods of the invention, the lipid or lipid composition may be administered to the subject by any method known in the art (e.g., those described herein). In certain embodiments, the composition is administered by a route selected from the group consisting of oral, rectal, parenteral (e.g., intravenously or intramuscularly), cutaneous, topical, nasal, vaginal, inhalant, skin (patch), and ocular.

By "enriched" is meant that a compound or substance is present in a composition at a level greater than found in nature, if the composition is naturally occurring. For example, a compound or substance may be enriched when it is present in an amount of at least 0.01%, 0.05%, 0.1%, 0.5%, 1%, 1.5%, 2%, 3%, 4%, 5%, 8%, 10%, 12%, 15%, 20%, 25%, 35%, 40%, 50%, 60%, 75%, 80%, 85%, 90%, 92%, 95%, 96%, 97%, 98%, 99%, or 100% of the total weight, or any range between these values, of the composition in which it is provided.

By "treating" is meant ameliorating at least one symptom of a condition or disease in a subject having the condition or disease (e.g., a subject diagnosed with a metabolic disorder), as compared with an equivalent untreated control. Such reduction in the symptom (e.g., a reduction in blood glucose levels) is at least 5%, 10%, 20%, 40%, 50%, 60%, 80%, 90%, 95%, or 100%, as measured by any standard technique.

By "treating prophylactically" is meant to reduce the frequency of disease occurrence or severity of disease upon its onset by administering to the subject a therapeutic prior to onset of the disease. Prophylactic treatment can include disease prevention. Subjects at higher risk of developing metabolic disorders or IBD (e.g., risk factors described herein) may be treated prophylactically in the methods of the invention.

By "inflammatory bowel disease" is meant an inflammatory condition of the small or large intestine. The major types of inflammatory bowel disease (IBD) are Crohn's disease and ulcerative colitis. Other forms of IBD include collagenous colitis, lymphocytic colitis, ischemic colitis, diversion colitis, Behçet's syndrome, infective colitis, and indeterminate colitis.

By "a metabolic disorder" is meant any pathological condition resulting from an alteration in a subject's metabolism. Such disorders include those resulting from an alteration in glucose homeostasis resulting, for example, in hyperglycemia. According to this invention, an alteration in glucose levels is typically an increase in glucose levels by at least 5%, 10%, 20%, 30%, 40%, 50%, 60%, 70%, 80%, 90%, or even 100% relative to such levels in a healthy individual. Metabolic disorders include obesity and diabetes (e.g., diabetes type I, diabetes type II, MODY, and gestational diabetes), satiety, and endocrine deficiencies of aging.

By "reducing glucose levels" is meant reducing the level of glucose by at least 10%, 20%, 30%, 40%, 50%, 60%, 70%, 80%, 90%, 95%, or 100% relative to an untreated control. Desirably, glucose levels are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL. Such reduction in glucose levels may be obtained by increasing any one of the biological activities associated with the clearance of glucose from the blood. Accordingly, an agent having the ability to reduce glucose levels may increase insulin production, secretion, or action. Insulin action may be increased, for example, by increasing glucose uptake by peripheral tissues and/or by reducing hepatic glucose production. Alternatively, the agent of the invention may reduce the absorption of carbohydrates from the intestines, alter glucose transporter activity (e.g., by increasing GLUT4 expression, intrinsic activity, or translocation), increase the amount of insulin-sensitive tissue (e.g., by increasing muscle cell or adipocyte cell differentiation), or alter gene transcription in adipocytes, liver, or muscle cells (e.g., altered secretion of factors from adipocytes expression of metabolic pathway genes). Desirably, the agent of the invention increases more than one of the activities associated with the clearance of glucose.

By "an amount sufficient" is meant an amount of a compound required to treat, treat prophylactically, or reduce disease or disorder (e.g., a metabolic disorder, such as diabetes, or IBD) in a clinically relevant manner. For example, a sufficient amount of an active compound used to practice the present invention for therapeutic treatment of conditions caused by or contributing to diabetes varies depending upon the manner of administration, the age, body weight, and general health of the subject. Ultimately, the prescribers will decide the appropriate amount and dosage regimen.

By "subject" is meant a human or non-human animal (e.g., a mammal).

By "increase" is meant an amount greater by at least 5%, 10%, 25%, 50%, 100%, 150%, 200%, 500%, or 1000%.

By "control subject" is meant a healthy subject or a subject not suffering from the disease or condition.

Other features and advantages of the invention will be apparent from the following Detailed Description, the drawings, and the claims.

BRIEF DESCRIPTION OF THE DRAWINGS

FIG. 3A shows that the mouse SHP promoter is activated by hLRH-1 and PCs. A 1080 bp portion of the 5'-flanking promoter region of the mSHP gene was linked to a luciferase reporter gene. HeLa cells were transfected with an hLRH-1 expression vector along with mSHP$_{1080}$-Luc reporter. Cells were treated with 100 μM of the indicated compounds. veh, ethanol solvent control; CDCA, chenodeoxycholic acid; DPPC, PC (16:0-16:0); DUPC, PC (11:0-11:0); DLPC, PC (12:0-12:0). FIG. 3B shows activation of the Oct4-PP by hLRH-1 and DUPC/DLPC. COS-1 cells were transfected with an hLRH-1 expression vector along with luciferase reporter gene containing the proximal promoter region (−417 to +35) of Oct4 gene (Oct4-PP Luc). Oct4-PPmut Luc is identical to Oct4-PP Luc except for the insertion of point mutations in the DR0 element. Mutation of the DR0 in the Oct4-PP eliminates activation by LRH-1 and DUPC/DLPC. FIG. 3C shows DUPC and DLPC selectively activate LRH-1 and SF-1. HeLa cells were cotransfected with various nuclear receptors and the reporter plasmid (RE-tk-luc). Cells were treated with either 100 μM DUPC or DLPC. Luciferase expression was assayed and normalized by β-galactosidase expression. Data are expressed for each reporter as fold activation of normalized luciferase activity relative to veh-treated cells. FIG. 3D shows DUPC/DLPC dose response for activation of a reporter gene by hLRH-1 in HeLa cells. Transfections were performed with 1, 10, 50, 100, 150, 200, or 250 μM of the indicated compounds and various NR5A expression vectors. EC$_{50}$ values were estimated to be 57 μM (DUPC) and 99 μM (DLPC) for hLRH-1.

FIG. 4A shows results from a mammalian two-hybrid assay performed in HeLa cells with VP16 alone or VP16-hLRH1 LBD along with Gal4-SRC3 receptor interaction domain (RID) in the presence of a Gal4 reporter (G5-tk-luc) and the indicated compounds. Data are expressed as fold activation of normalized luciferase activity relative to veh alone. FIG. 4B shows the GST pulldown assay was performed with GST alone or GST-hLRH-1 LBD along with in vitro translated coactivator [$^{35}$S] Met-SRC3 in the presence of 100 μM of the indicated compounds. CB, coomassie blue staining.

FIG. 5A shows Western blot analysis with anti-hLRH-1 antibody to confirm endogenous hLRH-1 knockdown using siRNA. C3A HepG2 cells (derivatives of HepG2) were transfected with either non-targeting siRNA control or siRNA hLRH-1. FIG. 5B shows compromised LRH-1 Luc promoter activity in siRNA hLRH-1 transfected C3A HepG2 cells. Increased LRH-1 Luc promoter activity is dependent on hLRH-1 and DUPC/DLPC in C3A HepG2. Cells were cotransfected with siRNA hLRH-1 (or siRNA control) and LRH-1 Luc reporter. Cells were treated with the indicated compounds 24 h after transfection. The luciferase assays were performed 48 h after transfection. FIG. 5C hCYP8B1 expression is induced by DUPC and DLPC in C3A HepG2 cells. Cells were transfected with either siRNA control or siRNA hLRH-1 followed by treatment of indicated compounds 24 h transfection. Cells were harvested 48 h after transfection to isolate total RNA. Gene expression was determined by Q-PCR. *$P<0.05$ vs Mock-veh.

FIG. 6A shows results from 8-week-old wild type male mice challenged orally with vehicle (ethanol in a 4:1 mixture of PEG-400 and Tween-80), CA, DPPC, DUPC, and DLPC (100 mg/kg body weight) five times in morning and evening over three days. Total liver RNA was isolated and prepared for the cDNA. Hepatic gene expression was determined using Q-PCR (n=5). *$P<0.05$ vs wt-veh. FIG. 6B shows results from 4-month-old LRH-1 homozygous flox male mice were injected with Ad-GFP ($3\times10^9$ pfu) or Ad-Cre ($3\times10^9$ pfu) through the tail vein. Two weeks later, those mice were challenged orally with vehicle, CA, DPPC, DUPC, and DLPC (100 mg/kg body weight) five times in morning and evening over three days. Total liver RNA was isolated and prepared for cDNA. Hepatic gene expression was determined using Q-PCR (n=4). *$P<0.05$, **$P<0.001$ vs LRH-1 f/f (Ad-GFP)-veh. FIG. 6C shows total, serum, and hepatic bile acids, and serum glucose and NEFA measured in the same control and treated animals. *$P<0.05$ vs wt-veh.

FIG. 8A shows results from 12-week-old male db/db mice (n=5) treated with vehicle, DPPC, or DLPC for 2 weeks. Glucose tolerance (GTT: 1.5 g/kg i.p.) was assessed in fasted mice. One week later, insulin tolerance (ITT: 2 U/kg i.p) was assessed in fed mice. In the ITT, glucose levels after insulin injection are presented as the percentage of initial glucose concentrations. FIG. 8B shows serum insulin, BAs, cholesterol, TG, and NEFA in the same control and treated animals. FIG. 8C shows hepatic TG, cholesterol, and NEFA in the same control and treated animals. FIG. 8D shows mRNA levels of lipogenic genes in the same control and treated animals. *$P<0.05$, **$P<0.01$ vs db-veh.

DETAILED DESCRIPTION

We have discovered that PC lipids having 22-24 carbons in their fatty acid tails, e.g., diundecanoyl (C11:0-C11:0) and dilauroyl (C12:0-C12:0) phosphatidylcholine (DUPC and DLPC, respectively) are capable of acting as agonists of the LRH-1 receptor. Diabetic mice receiving DUPC or DLPC orally exhibit, among other effects, reduced blood glucose levels. On the basis of these observations, the present invention features compositions and methods useful in the treatment of metabolic disorders and inflammatory bowel disease.

Phosphatidylcholine Lipids

Figure 1:
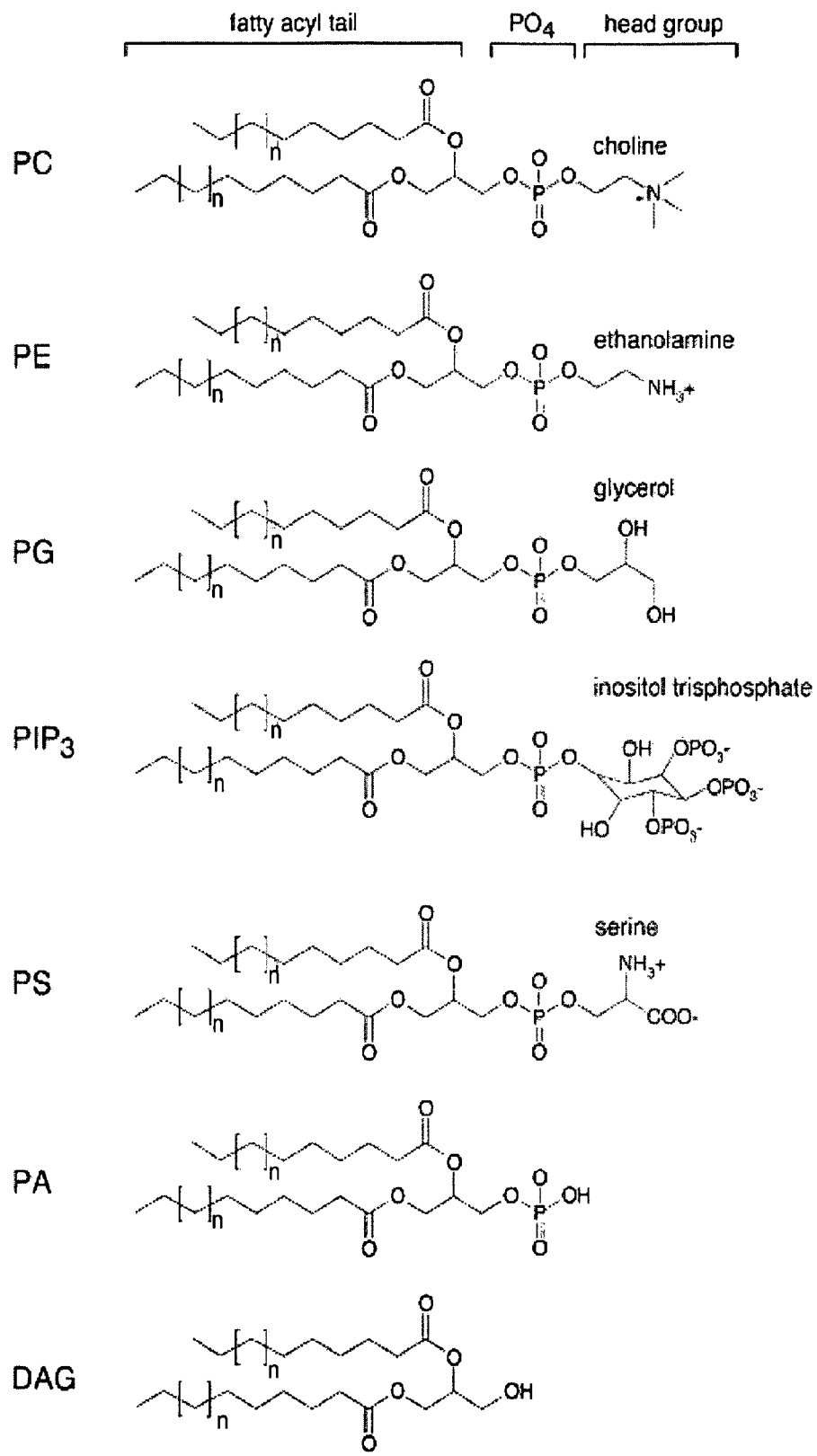
FIG. 1 is a set of diagrams showing generic phospholipid structures.

The lipids used in the compositions and methods of the invention have 22-24 carbon atoms in their fatty acid tails, where typically each tail has 10, 11, 12, or 13 carbon atoms. We have tested two compounds, DUPC and DLPC, which are phosphatidylcholine compounds having 11 and 12 carbon atoms, respectively, in each of the fatty acid tails on the molecules. General phospholipid structures are shown in FIG. 1. DUPC has the structure:

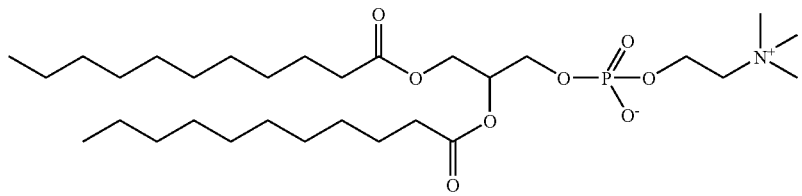 [SMILES: CCCCCCCCCCC(=O)OCC(COP(=O)([O-])OCC[N+](C)(C)C)OC(=O)CCCCCCCCCC]

DLPC has the structure:

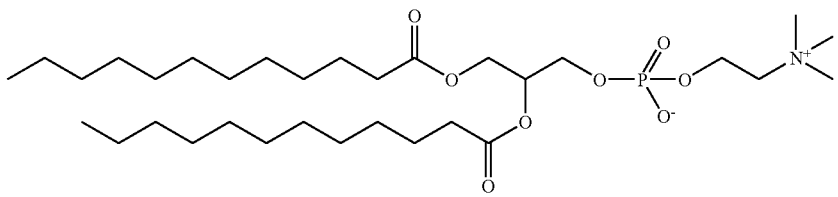 [SMILES: CCCCCCCCCCCC(=O)OCC(COP(=O)([O-])OCC[N+](C)(C)C)OC(=O)CCCCCCCCCCC]

Other PC lipids include C11:0, C12:0 undecanoyl, lauroyl PCs in particular, as well as C11:0, C13:0 undecanoyl, tridecanoyl PCs and C10:0, C12:0 decanoyl, lauroyl PCs.

The compositions of the invention may include one or more of these lipids, which may be present in amount(s) of at least 1, 5, 10, 25, 50, 100, 250, 500, or 750 µg; at least 1, 2, 5, 10, 25, 50, 100, 250, 500, or 750 mg; or at least 1, 2, 5, 10, 15, 20, 25, 50, or 100 g, or any range between these values. The compositions may include at least 0.01%, 0.05%, 0.1%, 0.5%, 1%, 2%, 3%, 5%, 8%, 10%, 15%, 20%, 25%, 40%, 50%, 60%, 75%, 85%, 90%, 95%, 98%, or 99% of the lipid(s), or any range between these values. In certain embodiments, the compositions include less than 99%, 98%, 95%, 90%, 85%, 75%, 60%, 50%, 40%, 25%, 20%, 15%, 8%, 5%, 3%, 2%, 1%, or 0.5% of the lipid(s). In compositions containing two or more lipids, the ratio between any two of the lipids present may be at least 1000:1, 500:1, 100:1, 50:1, 25:1, 10:1, 5:1, 3:1, 2:1, 1:1, 1:2, 1:3, 1:5, 1:10, 1:25, 1:50, 1:100, 1:500, or 1:1000, or any range between these values.

The compositions of the invention may be in any of the forms described herein. In some embodiments, the composition is food that has been enriched with one or more of these lipids. As described below, these lipids, or compositions containing these lipids, can be used to treat metabolic disorders (e.g., diabetes and obesity) and inflammatory bowel disease.

LRH-1 Molecular Biology

The NR5A nuclear receptors are a highly conserved subgroup of the nuclear receptor superfamily, with clear orthologs in *Drosophila* (FtzF1, NR5A4) (Lavorgna et al. Science 252:848-51, 1991; Broadus et al. Mol Cell 3:143-9, 1999), zebrafish (ff1b, NR5A3), and many other species. Mammalian NR5A2 was independently isolated by several groups and has been given multiple names (Nitta et al. Proc Natl Acad Sci USA 96:6660-5, 1999; Becker-Andre et al. Biochem Biophys Res Commun 194:1371-9, 1993; Galarneau et al. Mol Cell Biol 16:3853-65, 1996; Li et al. J Biol Chem 273:29022-31, 1998), but is now generally referred to as LRH-1 (Liver Receptor Homolog-1). It is closely related to SF-1 (NR5A1). Both receptors bind DNA as monomers, recognizing a shared consensus sequence (5'-(T/C)(C/A)AAGGX(C/T)X-3') consisting of the normal receptor binding hexamer with a 5' extension. A crystal structure of the LRH-1 DNA binding domain with its monomeric site (Solomon et al. J Mol Biol 354:1091-102, 2005) shows that the P box helix interacts with the major groove of the hexamer, as in other nuclear receptors, while a conserved C-terminal extension of the DNA binding domain termed the FtzF1 box (Ueda et al. Mol Cell Biol 12:5667-72, 1992) contacts the minor groove of the upstream (T/C)(T/C)A motif.

LRH-1 is expressed in adult tissues of endodermal origin including liver, gut, exocrine pancreas, and also ovary and testis (Bookout et al. Cell 126:789-99, 2006; Pare et al. J Biol Chem 279:21206-16, 2004; Schoonjans et al. Proc Natl Acad Sci USA 102:2058-62, 2005; Falender et al. Endocrinology 144:3598-610, 2003). In standard cotransfections it generally shows modest, apparently constitutive transactivation. In certain promoter contexts, LRH-1 alone is not enough to activate transcription and it instead functions as a competence factor to enhance promoter activity driven by other transcription factors (Lu et al. Mol Cell 6:507-15, 2000; Galarneau et al. Mol Cell Biol 16:3853-65, 1996; Iwaki et al. Diabetes 52:1655-63, 2003; Robert et al. Mol Cell Endocrinol 257-258:65-74, 2006; Matsukuma et al. J Biol Chem, 2007). Consistent with this, there are relatively few reports on the direct interaction of LRH-1 with coactivators, but interactions with SRC/p160 family members and PGC-1α have been reported (Ortlund et al. Nat Struct Mol Biol 12:357-63, 2005; Lee et al. J Biol Chem 277:2463-7, 2002, and see below).

In contrast to the apparently weak interaction with known coactivators, LRH-1 shows a strong interaction with the orphan receptor SHP (NR0B2), which acts as a corepressor (Goodwin et al. Mol Cell 6:517-26, 2000; Lu et al. Mol Cell 6:507-15, 2000; Lee et al. J Biol Chem 277:2463-7, 2002). Crystal structure analysis defined the interaction between LRH-1 and LxxLL motifs in SHP and explained the preference of SHP for interaction over other coregulators (Ortlund et al. Nat Struct Mol Biol 12:357-63, 2005; Li et al. Proc Natl Acad Sci USA 102:9505-10, 2005). It is thought that SHP is an important negative regulator of LRH-1 activity.

Like other nuclear hormone receptors, including its relative SF-1, the transcriptional activity of LRH-1 is modulated by posttranslational modification. The two major modifications identified are sumoylation (Chalkiadaki et al. Mol Cell Biol 25:5095-105, 2005) and phosphorylation (Lee et al. J Biol Chem 281:7850-5, 2006), which have opposite effects. SUMO modification of the hinge region localizes LRH-1 to promyelocytic leukemia protein (PML) nuclear bodies, excluding the transcription factor from active chromatin (Chalkiadaki et al. Mol Cell Biol 25:5095-105, 2005). The major sumoylation site ($Lys^{224}$; $Lys^{270}$ on hLRH-1 variant 1) is present in SF-1 at $Lys^{194}$, and the underlying repression mechanism also appears conserved (Chen et al. J Biol Chem 279:38730-5, 2004; Lee et al. Mol Cell Biol 25:1879-90, 2005). In contrast, phosphorylation of non-conserved sites on the two proteins enhances their transcriptional activities. Serines 238 and 243 in the hinge domain of human LRH-1 can be phosphorylated by protein kinase C (PKC) dependent pathways (Lee et al. J Biol Chem 281:7850-5, 2006). $Ser^{469}$ in the LBD has also been suggested as a potential target for protein kinase A-dependent activation of the human aromatase PII promoter (Bouchard et al. Endocrinology 146:4905-16, 2005). Activation of LRH-1 by PKC or PKA dependent pathways appears to be tissue specific because direct activation of mLRH-1 by these two pathways has not been observed in different tissue systems (Clyne et al. J Biol Chem 277:20591-7, 2002). In the case of SF-1, a distinct residue not conserved in LRH-1 ($Ser^{203}$) is phosphorylated, thereby stabilizing the protein and enhancing coactivator recruitment (Hammer et al. Mol Cell 3:521-6, 1999).

Physiologic Roles of LRH-1: Development and Bile Acid/Cholesterol Homeostasis

The first suggested physiological role of LRH-1 was in expression of $\alpha_1$-fetoprotein, an albumin gene family member that is a marker of endodermal specification during early liver development (Galarneau et al. Mol Cell Biol 16:3853-65, 1996). A broader association with endodermal differentiation emerged from the reciprocal observations that the mouse LRH-1 gene promoter has binding sites for transcription factors important for endodermal determination and hepatic differentiation, such as GATA, Nkx, and HNF4α, and that LRH-1 in turn contributes to expression of genes encoding transcription factors critical to early hepatic differentiation, such as Hnf3β/FoxA2, HNF4α, and Hnf1α (Pare et al. J Biol Chem 276:13136-44, 2001).

Another very early developmental function of LRH-1 is its ability to activate expression of Oct4, which is required to maintain pluripotence at the earliest stages of both embryonic development and ES cell differentiation (Gu et al. Mol Cell Biol 25:3492-505, 2005). The importance of LRH-1 in the initial stages of development is suggested by its broad expression in the early embryo and confirmed by the very early embryonic lethalilty of homozygous LRH-1 knockout mice (Botrugno et al. Mol Cell 15:499-509, 2004; Gu et al. Mol Cell Biol 25:3492-505, 2005; Pare et al. J Biol Chem 279: 21206-16, 2004).

LRH-1 mRNA is relatively abundant in ovary (Bookout et al. Cell 126:789-99, 2006; Falender et al. Endocrinology 144:3598-610, 2003; Boerboom et al. Endocrinology 141: 4647-56, 2000; Schoonjans et al. EMBO Rep 3:1181-7, 2002; Liu et al. Biol Reprod 69:508-17, 2003). This appears to be confined to granulosa cells, corpus luteum, and luteinized follicles, where the ovarian steroid hormones are synthesized by cytochrome P450 steroid hydroxylases. Aromatase, which converts androgens into estrogens, and the side chain cleavage enzyme ($P450_{sec}$), which catalyses the conversion of cholesterol to pregnenolone, have been proposed as potential ovarian LRH-1 target genes, suggesting a regulatory role for LRH-1 in ovarian steroidogenesis (Clyne et al. J Biol Chem 277:20591-7, 2002; Kim et al. J Clin Endocrinol Metab 90:1678-85, 2005).

The role of LRH-1 in the liver has been best characterized as a key regulator of cholesterol-7a hydroxylase (Cyp7A1), which is well known as the first and rate-limiting enzyme in the classic or neutral pathway of bile acid biosynthesis. Tight control of Cyp7A1 gene expression is very important to maintain appropriate levels of potentially toxic bile acids, and also to control cholesterol catabolism, since biliary elimination is the major pathway for cholesterol efflux from the body (Russell, D W Cell 97:539-42, 1999). A number of cotransfection and mutagenesis studies have suggested that LRH-1 is essential for proper Cyp7A1 promoter activity (Nitta et al. Proc Natl Acad Sci USA 96:6660-5, 1999; Goodwin et al. Mol Cell 6:517-26, 2000; Lu et al. Mol Cell 6:507-15, 2000). This is supported by in vivo results. Thus, in mice carrying an LRH-1 transgene controlled by the zinc inducible metallothionein I promoter, Cyp7A1 gene expression was clearly stimulated 6 hours after zinc injection (Pare et al. J Biol Chem 279:21206-16, 2004). A similar effect was observed at a relatively early time point (48 h) after infection with an adenoviral LRH-1 expression vector (Delerive et al. Mol Endocrinol 18:2378-87, 2004). However, Cyp7A1 gene expression was increased, rather than decreased as expected in heterozygous LRH-1 null mice (Pare et al. J Biol Chem 279:21206-16, 2004; del Castillo-Olivares et al. J Biol Chem 279:16813-21, 2004), and was also decreased at later time points (3-5 days) after adenoviral LRH-1 overexpression (Delerive et al. Mol Endocrinol 18:2378-87, 2004).

The role of LRH-1 as a positive regulator of expression of the orphan receptor SHP (Lee et al. J Biol Chem 274:20869-20873, 1999) can explain at least some of these discrepancies. In an elegant nuclear receptor cascade, LRH-1 (Lee et al. J Biol Chem 274:20869-20873, 1999) combines with the bile acid receptor FXR (Goodwin et al. Mol Cell 6:517-26, 2000; Lu et al. Mol Cell 6:507-15, 2000) to activate SHP expression when bile acid levels are elevated. This results in potent inhibition of Cyp7A1 expression via repression of transactivation by LRH-1, HNF4α, and potentially other targets, and thus in the normalization of bile acid levels. Based on this cascade, it is apparent that the level of LRH-1 expression is only one of several factors that control Cyp7A1 expression.

Moreover, this "simple" LRH-1-FXR-SHP loop is only one of several regulatory inputs in the increasingly complex area of bile acid homeostasis. Thus, SHP is also required for the negative regulation of Cyp7A1 expression in response to fibroblast growth factor 15/19 activation of its receptor FGFR4 (Inagaki et al. Cell Metab 2:217-25, 2005). In this loop, FXR activation in the gut results in increased FGF-15/19 expression and decreased hepatic bile acid production. The existence of SHP-independent pathways of bile acid effects was demonstrated by the ability of dietary bile acids, but not synthetic FXR ligands, to repress Cyp7A1 expression in SHP null mice (Wang et al. J Biol Chem 278:44475-81, 2003; Kerr et al. Dev Cell 2:713-20, 2002). Additional regulators that modulate Cyp7A1 expression include glucocorticoids, thyroid hormone, insulin, and circadian rhythm (Lavery et al. Genes Dev 7:1871-84, 1993; Crestani et al. J Lipid Res 36:2419-32, 1995; Chiang J Y Front Biosci 3:D176-93, 1998).

Very recently, Mataki et al. combined an albumin promoter/Cre-ER transgene with a floxed LRH-1 allele to produce a liver specific knockout of LRH-1 (Mataki et al. Mol Cell Biol, 27:8330-9, 2007). Due to leaky activity of the Cre-ER fusion, LRH-1 expression was essentially lost prior to tamoxifen activation, but mice were viable with no overt phenotypic changes. There were no substantial alterations in basic metabolic parameters such as serum or liver lipids, but the total bile acid pool was modestly decreased. Cyp7A1 expression was unaltered, not decreased as expected, apparently as a consequence of the concomitant decrease in SHP expression and/or input of other regulatory pathways. Instead, the major alteration in bile acid enzymes was a nearly complete loss of expression of another LRH-1 target (del Castillo-Olivares et al. J Biol Chem 275:17793-9, 2000) cholesterol 12α-hydroxylase, Cyp8B1. As expected, this was associated with a substantial decrease in its product, muricholic acid. Similarly, Lee et al. used albumin-cre and villin-cre to specifically delete LRH-1 in liver and intestine (Lee et al. Mol Endocrinol 22:1345-56, 2008). The loss of LRH-1 in the liver again led to a marked decrease in expression of Cyp8B1, but not Cyp7A1. Interestingly, the loss of hepatic LRH-1 did not prevent Cyp7A1 repression by the synthetic FXR agonist GW4064 (Lee et al. Mol Endocrinol 22:1345-56, 2008). This contrasts with the idea that SHP primarily targets LRH-1 to repress Cyp7A1 in response to FXR activation, but is in accord with evidence that it can repress other Cyp7A1 activators such as HNF-4α (Lee et al. Mol Cell Biol 20:187-95, 2000). Loss of intestinal LRH-1 expression decreased expression of SHP and the FXR targets IBABP and FGF-15 and did not affect gut intestinal morphology (Lee et al. Mol Endocrinol 22:1345-56, 2008).

LRH-1 has also been reported to directly regulate hepatic or intestinal expression of a number of additional enzymes and transporters involved in cholesterol and bile acid metabolism, including cholesteryl ester transfer protein (CETP), scavenger receptor class B type I (SR-BI), apical sodium-dependent bile acid transporter (ASBT), and apolipoprotein AI (ApoAI) (Schoonjans et al. EMBO Rep 3:1181-7, 2002; Delerive et al. Mol Endocrinol 18:2378-87, 2004; del Castillo-Olivares et al. J Biol Chem 275:17793-9, 2000; Inokuchi et al. J Biol Chem 276:46822-9, 2001; Bohan et al. J Biol Chem 278:36688-98, 2003; Luo et al. J Biol Chem 276:24767-73, 2001; Chen et al. J Biol Chem 278:19909-16, 2003). All of these genes contain one or more LRH-1 response elements in their promoters and are regulated positively by LRH-1. ApoAI, an initiator of HDL biogenesis, functions as an acceptor molecule for phospholipids and cholesterol effluxed from peripheral tissues to form pre-HDL particles. Mature HDL particles are transported into hepatocytes via the SR-BI receptor. In an alternative pathway, cholesteryl esters from HDL in plasma can be transferred to apolipoprotein B-containing lipoproteins to form VLDL by CETP, and taken up by the liver through LDL receptors. The involvement of multiple LRH-1 targets in reverse cholesterol transport and its downstream elimination via bile acid suggests an important function in cholesterol homeostasis. Additional roles of LRH-1 in bile acid homeostasis are confirmed by its regulation of BSEP, which effluxes bile acids from heptocytes into the bile ducts (Song et al. J Lipid Res 49:973-84, 2008), ASBT, which imports bile acids into intestinal enterocytes, and Mrp3, a basolateral transporter that promotes bile acid efflux from hepatocytes (Inokuchi et al. J Biol Chem 276:46822-9, 2001; Bohan et al. J Biol Chem 278: 36688-98, 2003; Chen et al. J Biol Chem 278:19909-16, 2003). In both liver specific LRH-1 knockout mice, expression of Mrp3 was decreased, along with that of the hepatic uptake and export transporters NTCP and BSEP (Mataki et al. Mol Cell Biol, 27:8330-9, 2007; Lee et al. Mol Endocrinol 22:1345-56, 2008). Thus, it seems clear that LRH-1 is a major contributor to the complex network of bile acid and cholesterol homeostasis. Particularly considering the recent identification of fatty acid synthase (FAS) as an additional target (Matsukuma et al. J Biol Chem 282: 20164-71, 2007), it is very likely that LRH-1 affects other lipid metabolic pathways.

Metabolic Disorders

The lipids and compositions containing these lipids described herein may be used to treat (e.g., prophylactically treat) metabolic disorders. These methods are particularly useful for treating subjects having or at risk of having any condition that is characterized by a state of hyperglycemia, which may be caused, for example, by an alteration in the insulin signaling pathway (e.g., a reduction in insulin production, resistance to insulin, or both). Exemplary disorders amenable to treatment according to this invention are obesity, diabetes (e.g., type 1 diabetes, type 2 diabetes, maturity-onset diabetes of the young (MODY), and gestational diabetes), satiety, endocrine deficiencies of aging, and any of their associated complications (e.g., Syndrome X, diabetic retinopathy, diabetic nephropathy, diabetic neuropathy, peripheral vascular disease, hyperlipidemia, hypertension, atherosclerosis, and coronary heart disease).

Diagnosis of Metabolic Disorders

The lipids and compositions containing these lipids are useful for treating a subject that has been diagnosed with, or is at risk of having a metabolic disorder, such as diabetes (e.g., type I or type II diabetes). A subject in whom the development of a metabolic disorder (e.g., diabetes or obesity) is being treated prophylactically (e.g., prevented) may or may not have received such a diagnosis. One in the art will understand that subjects may have been tested using standard tests or may have been identified, without examination, as one at high risk due to the presence of one or more risk factors (e.g., those described herein).

Diagnosis of metabolic disorders may be performed using any standard method known in the art, such as those described herein. Methods for diagnosing diabetes are described, for example, in U.S. Pat. No. 6,537,806, hereby incorporated by reference. Diabetes may be diagnosed and monitored using, for example, urine tests (urinalysis) that measure glucose and ketone levels (products of the breakdown of fat); tests that measure the levels of glucose in blood; glucose tolerance tests; and assays that detect molecular markers characteristic of a metabolic disorder in a biological sample (e.g., blood, serum, or urine) collected from the mammal (e.g., measurements of hemoglobin A1c (HbA1c) levels in the case of diabetes).

Subjects may be diagnosed as being at risk or as having diabetes if a random plasma glucose test (taken at any time of the day) indicates a value of 200 mg/dL or more, if a fasting plasma glucose test indicates a value of 126 mg/dL or more (after 8 hours), or if an oral glucose tolerance test (OGTT) indicates a plasma glucose value of 200 mg/dL or more in a blood sample taken two hours after a person has consumed a drink containing 75 grams of glucose dissolved in water. The OGTT measures plasma glucose at timed intervals over a 3-hour period. Desirably, the level of plasma glucose in a diabetic subject that has been treated according to the invention ranges between 160 to 60 mg/dL, between 150 to 70 mg/dL, between 140 to 70 mg/dL, between 135 to 80 mg/dL, and preferably between 120 to 80 mg/dL.

Optionally, a hemoglobin A1c (HbA1c) test, which assesses the average blood glucose levels during the previous two to three months, may be employed. A person without diabetes typically has an HbA1c value that ranges between 4% and 6%. For every 1% increase in HbA1c, blood glucose levels increases by approximately 30 mg/dL and the risk of complications increases. Preferably, the HbA1c value of a subject being treated according to the present invention is reduced to less than 9%, less than 7%, less than 6%, and most preferably to around 5%. Thus, the HbA1c levels of the subject being treated are preferably lowered by 10%, 20%, 30%, 40%, 50%, or more relative to such levels prior to treatment.

Gestational diabetes is typically diagnosed based on plasma glucose values measured during the OGTT. Since glucose levels are normally lower during pregnancy, the threshold values for the diagnosis of diabetes in pregnancy are lower than in the same person prior to pregnancy. If a woman has two plasma glucose readings that meet or exceed any of the following numbers, she has gestational diabetes: a fasting plasma glucose level of 95 mg/dL, a 1-hour level of 180 mg/dL, a 2-hour level of 155 mg/dL, or a 3-hour level of 140 mg/dL.

Ketone testing may also be employed to diagnose type 1 diabetes. Because ketones build up in the blood when there is not enough insulin, they eventually accumulate in the urine. High levels of blood ketones may result in a serious condition called ketoacidosis.

The use of any of the above tests or any other tests known in the art may be used to monitor the efficacy of the present treatment. Since the measurements of hemoglobin A1c (HbA1c) levels is an indication of average blood glucose during the previous two to three months, this test may be used to monitor a subject's response to diabetes treatment.

Risk Factors for Developing a Metabolic Disorder

Subjects may be determined to be at high risk of developing a metabolic disorder due to the presence of one or more risk factors, such as family history, obesity, particular ethnicity (e.g., African Americans and Hispanic Americans), gestational diabetes or delivering a baby that weighs more than nine pounds, hypertension, having a pathological condition predisposing to obesity or diabetes, high blood levels of triglycerides, high blood levels of cholesterol, presence of molecular markers (e.g., presence of autoantibodies), and age (over 45 years of age). An individual is considered obese when their weight is 20% (25% in women) or more over the maximum weight desirable for their height. An adult who is more than 100 pounds overweight, is considered to be morbidly obese. Obesity is also defined as a body mass index (BMI) over 30 kg/m$^2$.

Inflammatory Bowel Disease

The lipids described herein and compositions containing these lipids may also be used to treat (e.g., prophylactically treat) inflammatory bowel disease (IBD), including, for example, Crohn's disease and ulcerative colitis. Other forms of IBD include collagenous colitis, lymphocytic colitis, ischemic colitis, diversion colitis, Behçet's syndrome, infective colitis, and indeterminate colitis. Loss of one copy of LRH-1 substantially increases susceptibility of mice to pathologic effects in the well studied mouse models of IBD based on treatments with either 2,4,6-trinitrobenzene sulfonic acid (TNBS) or the milder dextran sodium sulfate (DSS), and DSS induces particularly severe colitis in gut specific LRH-$1^{-/-}$ mice (Coste et al., Proc Natl Acad Sci USA 104:13098-103, 2007).

In addition, the intestine has been identified as a site of extra-adrenal glucocorticoid production (Cima et al. J Exp Med 200:1635-46, 2004), and LRH-1 drives expression of the steroidogenic P450s Cyp11A1 (cholesterol side-chain cleavage enzyme) and Cyp11B1 (steroid 11-β-monooxygenase) in the intestinal mucosa following inflammatory stimuli such as treatments with T cell activating anti-CD3 antibody, which induces LRH-1 expression (Mueller et al. J Exp Med 203: 2057-62, 2006; Coste et al., Proc Natl Acad Sci USA 104: 13098-103, 2007). This induction of Cyp11A1 and B1 would be expected to decrease inflammatory responses due to the well-known inhibitory effects of glucocorticoids. Careful regulation of intestinal immune responses is crucial to promote appropriate interactions with gut microflora and to avoid the inappropriate responses observed in inflammatory bowel disease (IBD). Indeed, both total LRH-$1^{-/+}$ heterozygous mice and villin cre generated gut specific LRH-$1^{-/-}$ knockouts show decreased corticosterone production and increased levels of the inflammatory cytokines IL-1β and IL-6 in the 2,4,6-trinitrobenzene sulfonic acid (TNBS) induced mouse model of inflammatory bowel disease (Coste et al., Proc Natl Acad Sci USA 104:13098-103, 2007). As expected, this is associated with increased pathologic effects, including edema, neutrophil infiltration, and necrosis. Provocatively, biopsies from human patients with either Crohn's disease or ulcerative colitis showed substantially decreased expression of both LRH-1 and its Cyp11A1 and Cyp11B1 targets (Coste et al., Proc Natl Acad Sci USA 104:13098-103, 2007). A decrease in this LRH-1 dependent anti-inflammatory input may thus contribute to these common and difficult to treat immune disorders, and suggest increased LRH-1 activity could have beneficial effects.

Based on these results, decreased LRH-1 activity is associated with IBD, thus suggesting that LRH-1 agonists, such as DUPC and DLPC, can be used to treat (e.g., treat prophylactically) this disorder.

Formulation of Pharmaceutical Compositions

The administration of a lipid or lipids described herein or a composition containing one or more of these lipids may be by any suitable means that results in a concentration of the compound that treats a metabolic disorder or IBD. The lipid may be in any appropriate amount of any suitable carrier substance, and is generally present in an amount of 1-95% by weight of the total weight of the composition. The composition may be provided in a dosage form that is suitable for the oral, parenteral (e.g., intravenously or intramuscularly), rectal, cutaneous, nasal, vaginal, inhalant, skin (patch), topical, ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Pharmaceutical compositions may be formulated to release the lipid(s) immediately upon administration or at any predetermined time or time period after administration. The latter types of compositions are generally known as controlled release formulations, which include (i) formulations that create substantially constant concentrations of the lipid(s) within the body over an extended period of time; (ii) formulations that after a predetermined lag time create substantially constant concentrations of the lipid(s) within the body over an extended period of time; (iii) formulations that sustain the lipid(s) action during a predetermined time period by maintaining a relatively constant, effective level of the lipid(s) in the body with concomitant minimization of undesirable side effects associated with fluctuations in the plasma level of the lipid(s) (sawtooth kinetic pattern); (iv) formulations that localize action of lipid(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the lipid(s) by using carriers or chemical derivatives to deliver the compound to a particular target cell type. Administration of the lipid(s) in the form of a controlled release formulation is especially preferred for lipid(s) having a narrow absorption window in the gastro-intestinal tract or a relatively short biological half-life.

Any of a number of strategies can be pursued in order to obtain controlled release in which the rate of release outweighs the rate of metabolism of the lipid(s) in question. In one example, controlled release is obtained by appropriate selection of various formulation parameters and ingredients, including, e.g., various types of controlled release compositions and coatings. Thus, the lipid(s) is formulated with appropriate excipients into a pharmaceutical composition that, upon administration, releases the lipid(s) in a controlled manner. Examples include single or multiple unit tablet or capsule compositions, oil solutions, suspensions, emulsions, microcapsules, molecular complexes, microspheres, nanoparticles, patches, and liposomes.

Solid Dosage Forms for Oral Use

Formulations for oral use include tablets containing the lipid(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the lipid(s) in a predetermined pattern (e.g., in order to achieve a controlled release formulation) or it may be adapted not to release the lipid(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes (e.g., chemical degradation prior to the release of the active substances). The coating may be applied on the solid dosage form in a similar manner as that described in Encyclopedia of Pharmaceutical Technology, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the lipid(s) is mixed with an inert solid diluent (e.g., potato starch, lactose, microcrystalline cellulose, calcium carbonate, calcium phosphate, or kaolin), or as soft gelatin capsules wherein the lipid(s) is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

Dosages

The dosage of lipid(s) contained in a composition described herein or used in the methods described herein depends on several factors, including: the administration method, the disorder to be treated, the severity of the disorder, whether the disorder is to be treated or prevented, and the age, weight, and health of the subject to be treated. In certain embodiments, an adult human subject may receive between 0.1 and 100 g/day (e.g., about 0.1, 0.2, 0.5, 1.0, 2.0, 3.0, 4.0, 5.0, 6.0, 7.0, 8.0, 9.0, 10, 12, 15, 20, 30, 40, 50, 60, 70, 80, 90, or 100 g/day) of the lipid or combination of lipids (e.g., 1-10 g/day).

With respect to the treatment methods of the invention, it is not intended that the administration of a compound to a subject be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat a metabolic disorder or IBD, to decrease blood glucose levels, or to increase LRH-1 receptor activation. The compound may be administered to the subject in a single dose or in multiple doses. For example, a compound described herein or identified using screening methods of the invention may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compound. For example, the dosage of a compound can be increased if the lower dose does not provide sufficient activity in the treatment of a metabolic disorder (e.g., diabetes or obesity). Conversely, the dosage of the compound can be decreased if the metabolic disorder is reduced or eliminated.

While the attending physician ultimately will decide the appropriate amount and dosage regimen, a therapeutically effective amount of a DUPC or DLPC may be, for example, in the range of 0.0035 µg to 1 g/kg body weight/day or 0.010 µg to 100 mg/kg body weight/week. For example, a therapeutically effective amount is in the range of 0.025 µg to 10 mg/kg body weight administered daily, every other day, or twice a week. In addition, a therapeutically effective amount may be in the range of 0.05 µg to 20 mg/kg, for example, at least 0.05, 0.1, 0.15, 0.2, 1, 2, 3, 5, 8, 10, 25, 50, 100, 200, or 500 µg/kg or 1, 2, 5, 8, 10, 15, or 20 mg/kg body weight administered one, two, three, or four times a day, one, two, three, or four times weekly, every other week, or once a month.

The following examples are meant to illustrate, rather than limit the invention:

EXAMPLE 1

Identification of LRH-1 Agonists

Figure 2A:
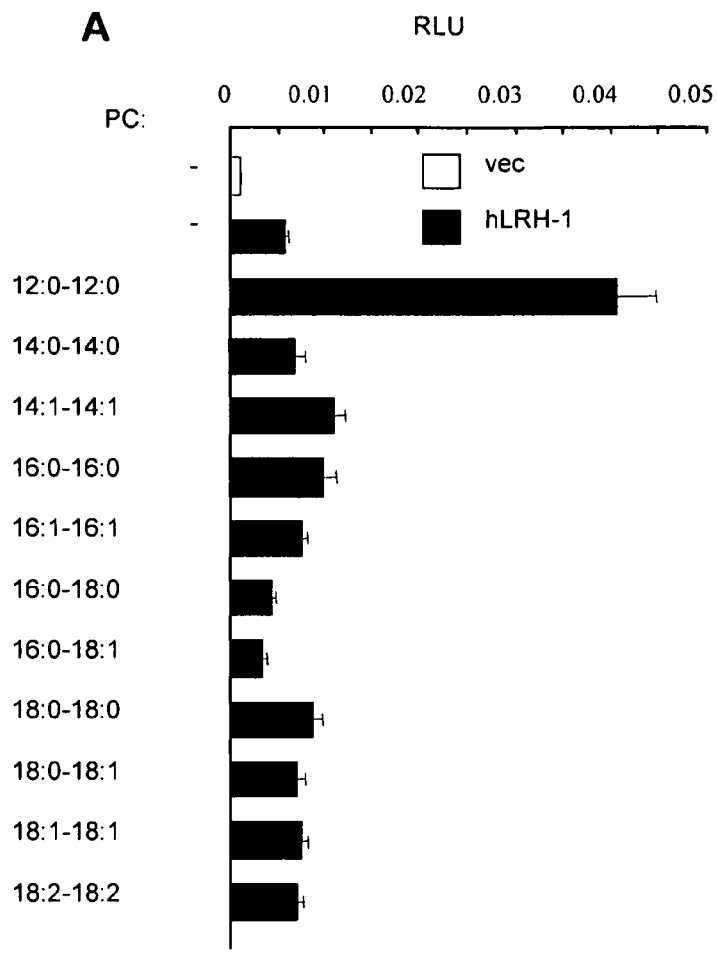
FIGS. 2A and 2B are graphs showing luciferase activity from HeLa cells transfected with a human LRH-1 (hLRH-1) expression vector and treated with the indicated phosphotidylcholines (PC). Controls (vector only and no lipid) are as indicated. The luciferase assay reporter carrying multiple LRH-1 binding sites (SF-1 Luc) has been described previously (Ikeda et al., Mol Endocrinol 7:852-60, 1993). Cells were treated with 100 μM of the indicated PCs and luciferase expression (RLU, relative light units) was normalized using an internal β-galactosidase control. vec, empty vector; –, ethanol solvent control.
Figure 2B:
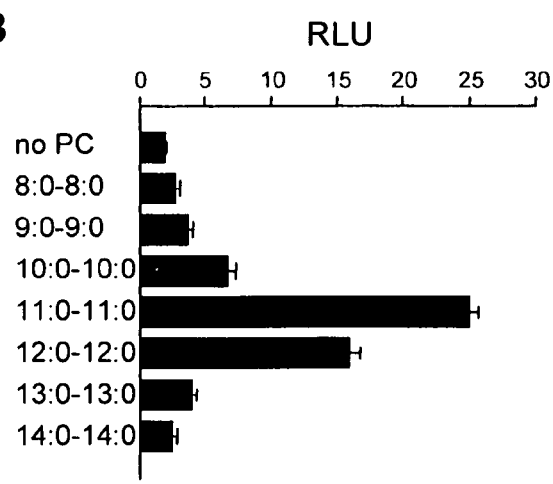

A number of different phosphatidylcholine (PC) species were screened for effects on human LRH-1 transactivation in HeLa cell cotransfections with a synthetic luciferase reporter containing multiple copies of an LRH-1/SF-1 response element. Most had little or no effect on the basal LRH-1 transactivation, but a substantial increase was observed for the double C12:0 PC dilauroyl phosphatidylcholine (DLPC) (FIG. 2A). This was confirmed in more focused analysis of shorter saturated chain lengths. This analysis also showed responses to DLPC, as well as to 0-C11:0 diundecanoyl PC (DUPC) (FIG. 2B).

Figures 3A, 3B, 3C, 3D:
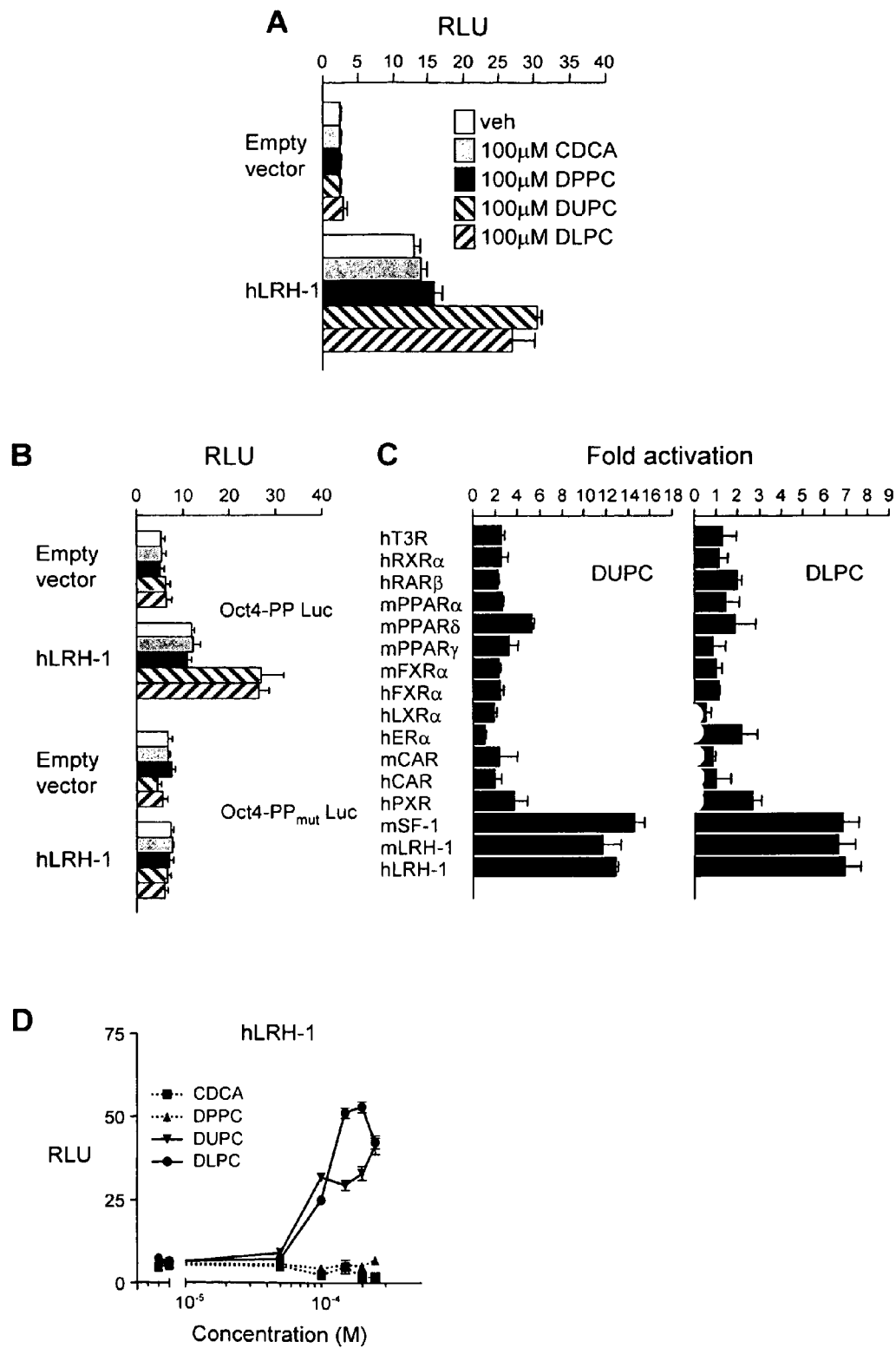
FIGS. 3A-3D are a set of graphs showing specific hLRH-1 activation by medium length PCs.

DUPC and DLPC induced similar, but lesser responses with this reporter in CV-1 and HEK293T cells, and also specifically increased LRH-1 transactivation of the native mouse SHP promoter by approximately 2-fold in HeLa cells (FIG. 3A). This is the same as the effect of the most potent synthetic LRH-1 agonist on the human SHP promoter (Whitby et al., J Med Chem 49:6652-5, 2006). DUPC and DLPC, but not the bile acid cholic acid (CA) or dipalmitoyl PC(C16:0-C16:0; DPPC), also induced a similar response with the Oct4 promoter. As expected for direct activation of the receptor, this response was dependent on both LRH-1 cotransfection and the presence of the single LRH-1 response element Gu et al., Mol Cell Biol 25:3492-505, 2005) (FIG. 3B).

In contrast to the prediction from the crystal structures, mouse and human LRH-1 show essentially equivalent responses to DUPC and DLPC. Both DUPC and DLPC also activate SF-1, with a response very similar to that of LRH-1. This activation is substantially greater than that observed with the recently described ligand C14:0-C14:0 PA (Li et al. Mol Cell Biol, 27:6669-6685, 2007), which increased SF-1 transactivation by only 1.2-1.4 fold in our hands and, as reported, had no effect on LRH-1 transactivation (FIG. 3C).

These effects are very specific for LRH-1 and SF-1. Neither DUPC nor DLPC showed significant effects on the internal control promoters used to normalize cotransfections, and they did not activate or inhibit any of a number of additional nuclear receptors tested, including TRβ, RARβ, RXRα, PPARα, PPARδ, PPARγ, FXR, LXRα, ERα, mouse or human CAR, and human PXR (FIG. 3C).

Also in contrast to crystal structure predictions of limited interaction between the receptor and the phospholipid head group, the LRH-1 response appears specific to PCs. We observed no activation with a number of PE species, including C10:0-10:0, C12:0-12:0, or C14:0-C14:0, or the analogous PA species (data not shown).

The $EC_{50}$ values for DUPC and DLPC activation of human LRH-1 are approximately 60 and 100 µM (FIG. 3D), and similar values were obtained for mouse LRH-1 and SF-1. While these concentrations are much higher than the estimated 100 nM affinity of SF-1 for C14:0-C14:0 PA (Li et al. Mol Cell Biol, 27:6669-6685, 2007), numerous issues including solubility, cell permeability and intracellular transport and turnover leave it impossible to directly compare the in vitro and cell based studies.

Based on these results, we believe that phosphatidylcholine species with total fatty acid chain lengths of between the 22 carbons of DUPC and the 24 carbons of DLPC, will also act as LRH-1 agonists. We believe compounds having 10, 11, 12, or 13 fatty acid chain lengths will be particularly useful. These compounds include, in particular, the C11:0, C12:0 undecanoyl, lauroyl PCs, as well as the C11:0, C13:0 undecanoyl, tridecanoyl PCs and the C10:0, C12:0 decanoyl, lauroyl PCs.

EXAMPLE 2

Characterization of DUPC and DLPC as LRH-1 Ligands

Figure 4A:
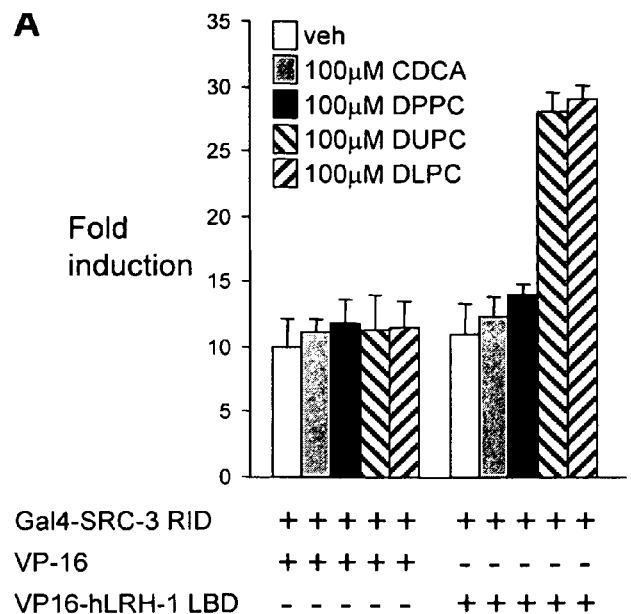
FIGS. 4A and 4B are a set of graphs and a photograph showing that DUPC and DLPC promote association of hLRH-1 and SRC-3 in vivo and in vitro.
Figure 4B:
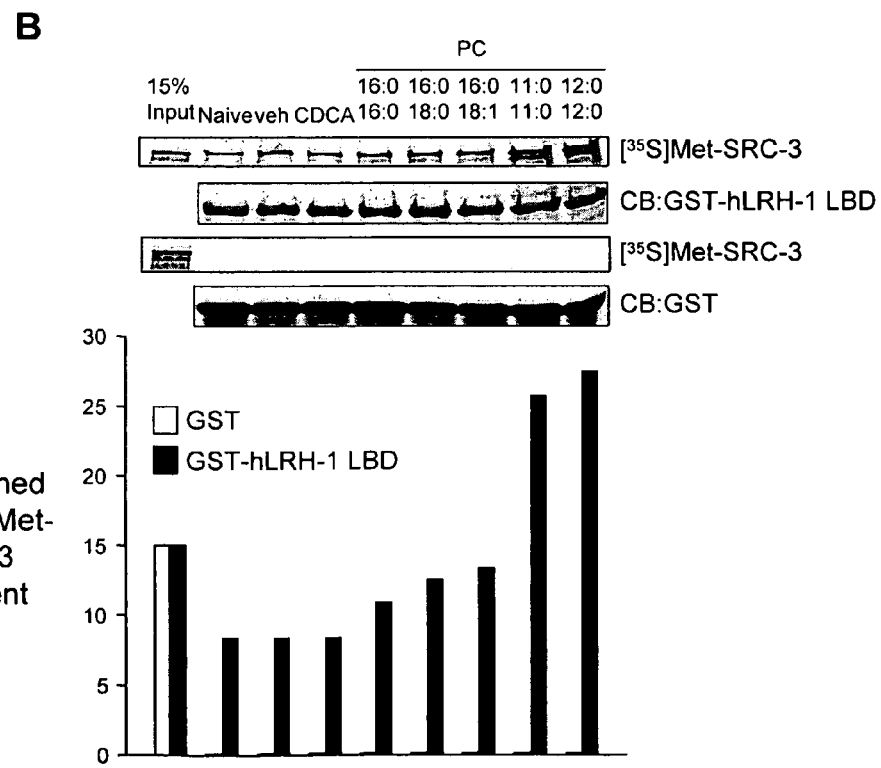

We used both the mammalian two-hybrid assay and a standard GST pulldown approach to address the presumed function of DUPC and DLPC as LRH-1 ligands. The mammalian 2-hybrid analysis tested the interaction of a VP16-human LRH-1 ligand binding domain fusion with a second fusion of the Gal4 DNA binding domain to the receptor interaction domain of the coactivator SRC-3. As expected, this interaction was unaffected by chenodeoxycholic acid (CDCA) or DPPC, but was stimulated by DUPC and DLPC (FIG. 4A). In the GST pulldown, the substantial basal interaction of E. coli expressed GST-LRH1 with in vitro translated $^{35}$S-labeled full length SRC-3 was further increased by either DUPC or DLPC, but not by DPPC or 2 other conventional PCs (FIG. 4B). Quantitative measurements using PhosphorImager® imaging device of these and additional results showed that both DUPC and DLPC reproducibly increase SRC-3 binding by approximately 3-fold, while the effect of other PCs is 1.5 fold or less. Based on these results and the extensive previous results demonstrating phospholipid binding to NR5A receptors, we conclude that DUPC and DLPC are LRH-1 agonists.

Figure 5A:
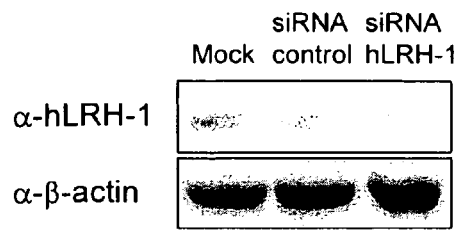
FIGS. 5A-5C are a photograph and a set of graphs showing that increased LRH-1 activity is dependent on hLRH-1 and DUPC/DLPC.
Figure 5B:
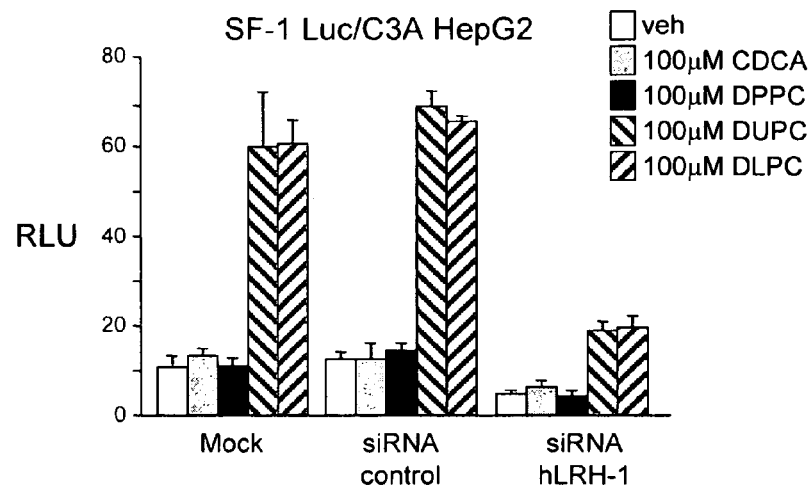
Figure 5C:
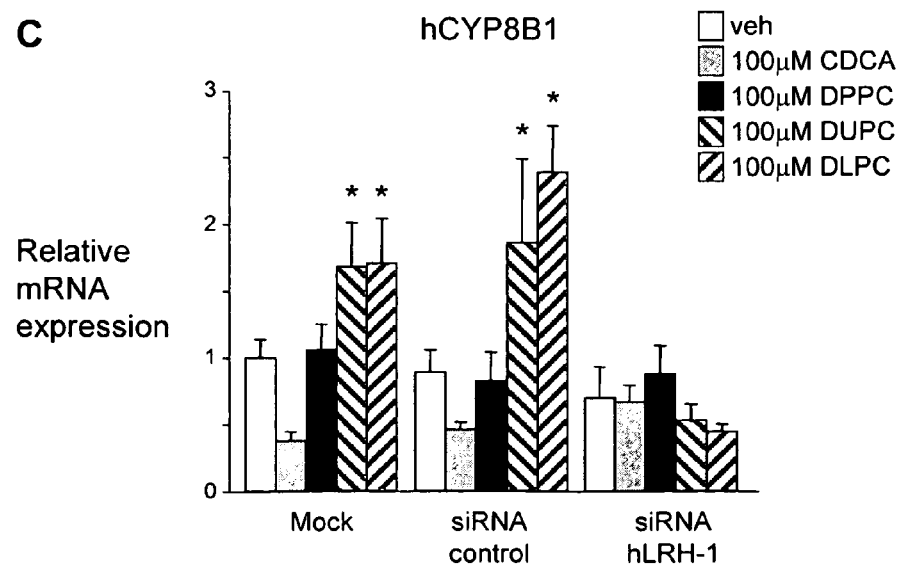

We have begun to address the impact of DUPC and DLPC on endogenous LRH-1 target genes in liver derived cell lines. By western blotting C3A derivative of HepG2 cells (unlike its parent) was observed to express intact LRH-1. This expression can be strongly decreased by a Dharmacon pool of siRNAs (FIG. 5A). In the C3A/HepG2 cells, or cells treated with non-target control siRNAs, DUPC and DLPC, but not DPPC with the luciferase promoter, increased luciferase was observed in cells receiving DUPC or DLPC, but not DPPC, CDCA, or vehicle. The absolute levels were reduced in cells treated with an hLRH-1 siRNA (FIG. 5B). In the C3A/HepG2 cells, or cells treated with non-target control siRNAs, DUPC and DLPC, but not DPPC, modestly but significantly induced expression of the LRH-1 target Cyp8B1, which was also repressed by CA as expected (FIG. 5C). Both the DUPC/DLPC and CA responses are lost when LRH-1 expression is knocked down. This is an important confirmation that DUPC and DLPC can activate endogenous LRH-1 to induce expression of a native target gene, and that this response is not dependent on hypothetical LRH-1 independent signaling pathways.

EXAMPLE 3

In Vivo Effects of DUPC and DLPC

Figures 6A, 6B, 6C:
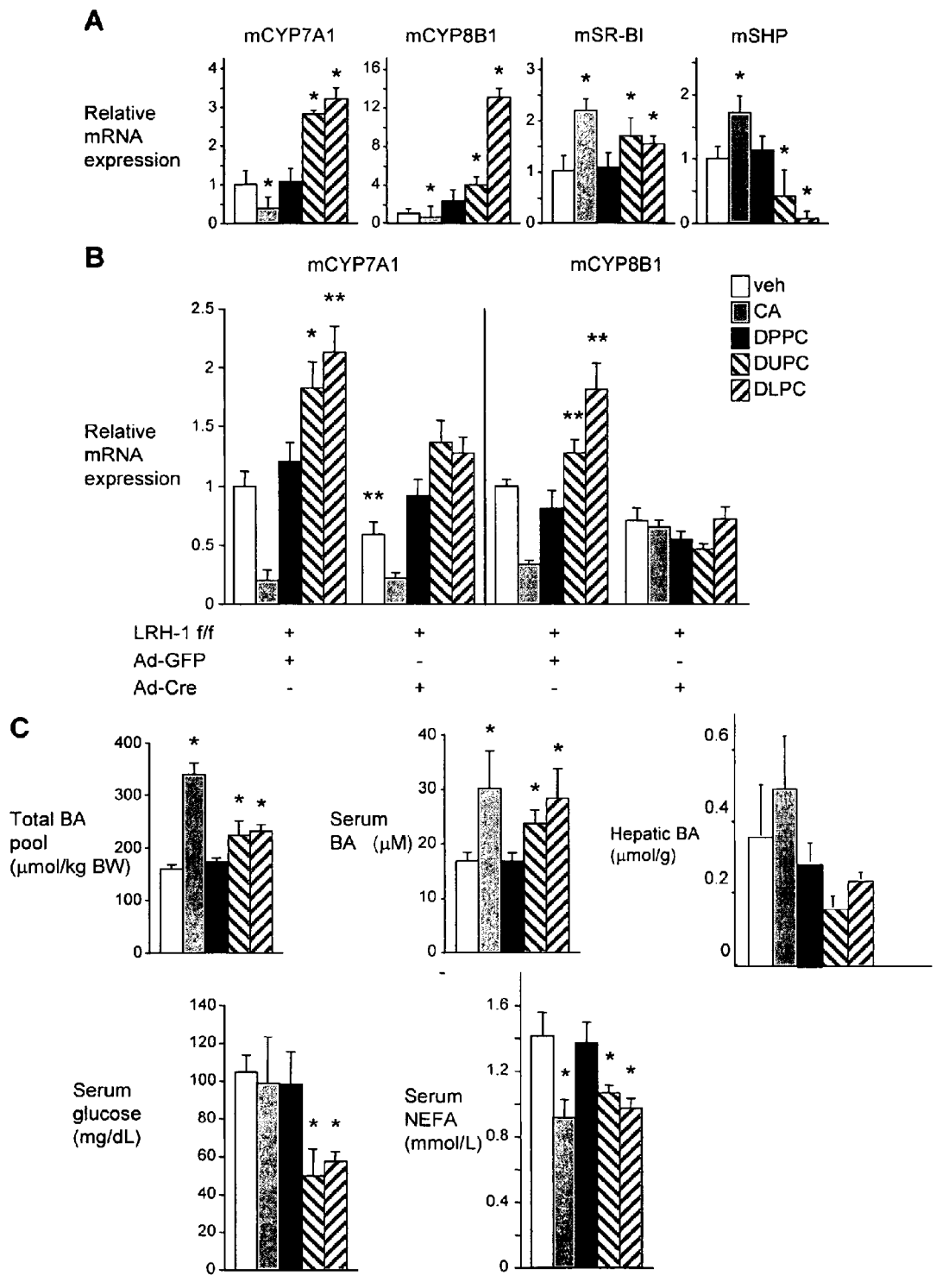
FIGS. 6A-6C are a set of graphs showing an animal study with DUPC/DLPC.

We used the simple route of oral gavage to deliver DUPC and DLPC to normal mice. As in the earlier experiments, CA served as a positive control for effects on bile acid synthetic genes and pool, and DPPC served as a negative control for effects on LRH-1. 8-week-old male mice received five treatments over a three day time course with vehicle (ethanol) or 100 mg/kg body weight of DPPC, DUPC, or DLPC. Compounds were administered in a PEG-400 and Tween-80 mixture (4:1), a cosolvent surfactant combination commonly used for oral delivery of hydrophobic nuclear receptor ligands (Mukherjee et al. Arterioscler Thromb Vasc Biol 18:272-6, 1998; Levin et al. Arterioscler Thromb Vasc Biol 25:135-42, 2005; Jung et al. J Lipid Res 48:2693-700, 2007). These treatments were not associated with any obvious toxicity, and did not alter liver weight or increase serum enzyme indicators of liver damage (ALT and AST). As expected, CA reduced expression of Cyp7A1 and Cyp8B1, and induced mSR-BI and SHP, while DPPC was without significant effect (FIG. 6A). Both DUPC and DLPC significantly induced expression of Cyp7A1, Cyp8B1, and mSR-BI, and repressed expression of SHP (FIG. 6A). The responses to DUPC and DLPC were not observed when the LRH-1 gene was removed by Cre, thus evidencing the involvement of the LRH-1 receptor (FIG. 6B). The substantial induction of Cyp8B1, particularly by DLPC, is in good accord with the opposite response in the liver specific LRH-1 knockouts (Mataki et al. Mol Cell Biol, 27:8330-9, 2007; Lee et al. Mol Endocrinol 22:1345-56, 2008). Increased levels of both Cyp7A1 and 8B1 are also consistent with the decreased SHP levels, although it might have been anticipated that SHP would have been induced. As noted above, the interplay among the different components of this regulatory loop is complex and time dependent, and can leading to conflicting results (Pare et al. J Biol Chem 279:21206-16, 2004; Delerive et al. Mol Endocrinol 18:2378-87, 2004; del Castillo-Olivares et al. J Biol Chem 279:16813-21, 2004). Importantly, these gene expression changes were associated with a significant increase in the total bile acid pool in the DUPC and DLPC treated mice (FIG. 6C). Liver bile acids appeared somewhat lower in DUPC and DLPC treated mice, but did not show statistically significant changes even in the CA fed mice, indicating the maintenance of overall hepatocyte bile acid homeostasis. Consistent with the activation of protective responses such as bile acid export from the liver, serum bile acid levels were substantially elevated by DUPC, DLPC, and CA (FIG. 6C). We (Ma et al. J Clin Invest 116:1102-9, 2006) and others (Zhang et al. Proc Natl Acad Sci USA 103:1006-11, 2006; Cariou et al. J Biol Chem 281:11039-49, 2006) have recently linked increased bile acid levels to improvements in lipid and glucose homeostasis. Consistent with this, both bile acid and DUPC/DLPC treated mice showed decreased levels of serum free fatty acids, and this was associated with decreased serum glucose levels in the DUPC/DLPC treated, but not the CA treated mice (FIG. 6C).

Figure 7:
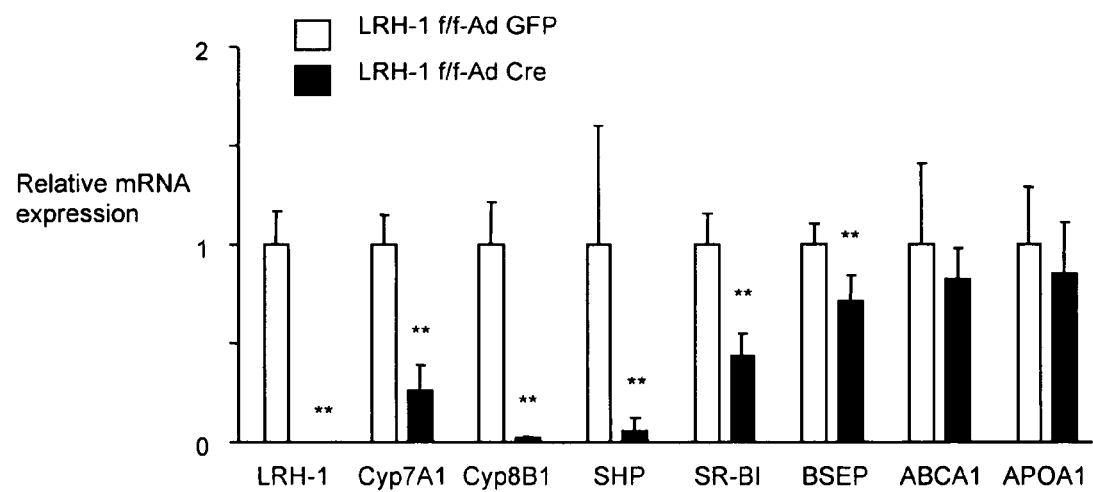
FIG. 7 is a graph showing effects of acute LRH-1 deletion in wild type mice. Two weeks after tail vein injection of 12-week-old male C57/B16 mice with the GFP or Cre expressing adenoviral vectors, total liver RNA was isolated and pooled from an average of six mice per group. Hepatic gene expression was determined using quantitative RT-PCR (n=6). **$P<0.01$ vs. Ad-GFP.

A crucial question is whether these results, like the induction of Cyp8B1 in C3A/HepG2 cells, are dependent on LRH-1. To answer this question, we have obtained the floxed (f/f) LRH-1 line from the Kliewer/Mangelsdorf lab at UT Southwestern and have preliminary results from mice infected with adenoviral cre or control GFP expression vectors. In an initial experiment in untreated mice two weeks after infection, LRH-1 mRNA was essentially eliminated and Cyp8B1 expression was also nearly absent (FIG. 7), as expected from the results with chronic liver specific knockouts (Mataki et al. Mol Cell Biol, 27:8330-9, 2007; Lee et al. Mol Endocrinol 22:1345-56, 2008). This acute deletion was also associated with decreased levels of Cyp7A1, which contrast with the results of the longer-term experiments, presumably due to compensatory effects in the chronic context that are not yet evident in the acute cre-mediated deletion. Decreased expression of additional LRH targets, including SHP, SR-B1, and BSEP, was also observed, but ABCA1 and ApoA1 were not decreased (FIG. 7). The decreased expression of the bile acid biosynthetic enzymes was associated with a very significant ($P<0.001$), approximately 50% decrease serum bile acid levels (data not shown). In a preliminary experiment with CA or PC treated mice, adenoviral-cre infection resulted in only a 60-70% loss of LRH-1 mRNA levels, which produced only a small decrease in the basal expression of Cyp8B1, but a significant decrease in basal expression of CY8A1 (FIG. 6B). Remarkably, however, the inductive response to DUPC and DLPC was completely absent in the adenoviral-cre infected livers (FIG. 6B). The repressive effect of dietary CA was also lost, which is consistent with the proposed role of LRH-1 as a major target of this effect, but contrasts with retention of the repressive effect of the synthetic FXR agonist GW4064 in the chronic albumin-cre liver specific knockouts (Lee et al. Mol Endocrinol 22:1345-56, 2008). These results strongly indicate that LRH-1 is the target of DUPC and DLPC effects in the liver.

EXAMPLE 4

DLPC Treatment in Diabetic Mice

Figures 8A, 8B, 8C, 8D:
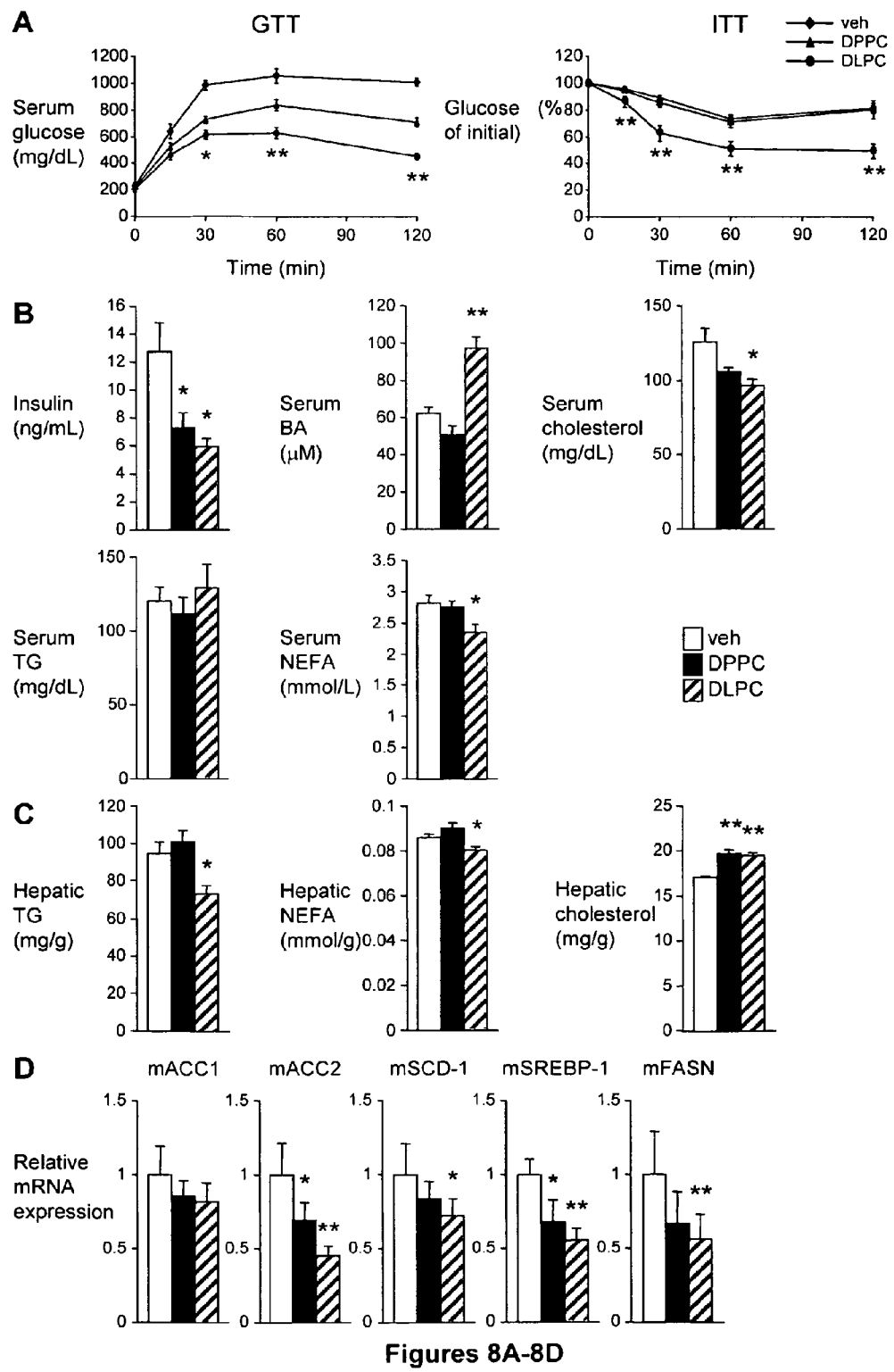
FIGS. 8A-8D are graphs showing improved diabetic conditions in mice upon administration of DLPC.

Prompted by these promising results, we treated insulin resistant, leptin receptor deficient db/db mice for 2 weeks with either DLPC or DPPC by oral gavage, followed by a glucose tolerance test (GTT). After 1 week of additional treatment, the same mice were given an insulin tolerance test (ITT) and sacrificed. The DLPC treated mice showed a remarkable improvement in glucose homeostasis in both the GTT and ITT (FIG. 8A).

DPPC treatment resulted in a lesser beneficial response in the GTT, but not the ITT. This effect was not anticipated, but is consistent with the demonstration of decreased total PC levels in human patients with non-alcoholic fatty liver disease or steatohepatitis (Puri et al. Hepatology 46:1081-90, 2007), with a report that dietary PC (egg derived, mainly C16:0, C18:1, and C18:2) nearly completely blocks the induction of fatty liver by the uridine precursor orotic acid (Buang et al. Nutrition 21:867-73, 2005), and also with an older study indicating that dietary PC decreases hepatic triglycerides in normal rats (Imaizumi et al. J Nutr 113:2403-11, 1983). A diet deficient in both methionine and choline is widely used to induce fatty liver in rodents, and both this and the response to orotic acid are linked to decreased levels of methyl donors (Griffin et al. Physiol Genomics 17:140-9, 2004). Synthesis of one molecule of PC from PE by phosphatidylethanolamine N-methyltransferase (PEMT) requires three methyl groups and is considered to be an important consumer of S-adenosylmethionine (Jacobs et al. J Biol Chem 280:28299-305, 2005). Consistent with this, total hepatic PC levels are decreased in mice on the methionine/choline deficient diet (Larter et al. J Hepatol 48:638-47, 2008). It therefore seems possible that a positive impact of supplementation with PC (or just choline) on the methyl donor pool could alter fatty acid metabolism and thereby contribute to the observed DPPC effect. Whether or not this is the case, the DLPC treated mice showed substantially more dramatic responses. Thus, the LRH-1 agonist has a strong beneficial impact on diabetes, which may include both a nonspecific effect related to PC/choline supplementation and a specific effect on LRH-1.

We have carried out initial studies to explore the basis of these beneficial effects of DLPC in these db/db mice. A number of parameters examined were not altered by DPPC or DLPC, including total body weight, or weight of liver or reproductive fat pads. As expected from the results in the wild type mice, serum bile acid levels were significantly increased by DLPC, but not DPPC, and DLPC also modestly decreased serum free fatty acids (NEFA) and cholesterol (FIG. 8B). Importantly, DLPC also significantly decreased hepatic triglycerides (TG) and more modestly lowered NEFA, and increased hepatic cholesterol (FIG. 8C). At the gene expression level, DLPC, but not DPPC, increased expression of Cyp7A1 and Cyp8B1, as expected. SR-B1 expression was not significantly affected by either (data not shown), and SHP expression appeared to be decreased by both, although this was not statistically significant. Rather surprisingly, there was also no effect on hepatic expression of a number of genes associated with glucose homeostasis, including acylCoA carboxylase (ACC1) (FIG. 8D), glucokinase, hexokinasel and 2, phosphoenolpyruvate carboxykinase (PEPCK), glucose-6-phosphatase, pyruvate carboxylase, and PGC-1α (data not shown). However, DLPC, and to a somewhat lesser extent DPPC, significantly decreased expression of the lipogenic transcription factor SREBP-1c, and its key downstream targets acylCoA carboxylase (ACC2), stearoyl CoA desaturase (SCD-1) and fatty acid synthase (FAS) (FIG. 8D). These results are consistent with the possibility that DLPC and potentially DPPC supplementation has a beneficial impact on fatty liver in this diabetic model, but does not directly alter hepatic glucose homeostasis. This suggests that non-hepatic tissues such as skeletal muscle may be responsible for the increased insulin sensitivity, which would be generally consistent with the results with bile acids and $FXR^{-/-}$ mice (Beil et al. J Lipid Res 21:525-36, 1980; Mukherjee et al. Arterioscler Thromb Vasc Biol 18:272-6, 1998; Levin et al. Arterioscler Thromb Vasc Biol 25:135-42, 2005).

Figure 9:
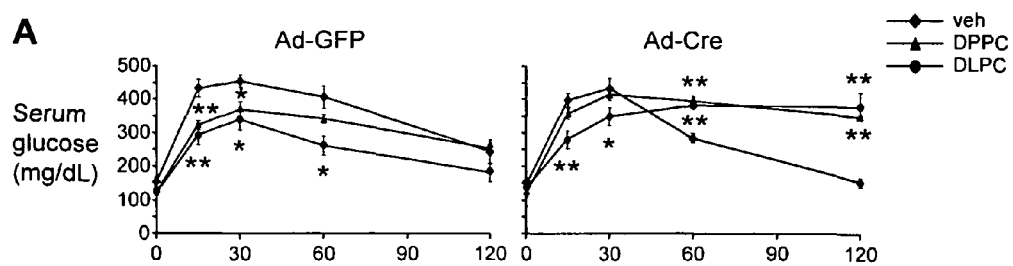
FIG. 9 is a set of graphs showing that the antidiabetic effects of DLPC are LRH-1 dependent. 8-10 week-old male LRH-1 f/f littermates were injected with either Ad-GFP or Ad-Cre. Starting 2 weeks after infection, mice were fed a 45% high fat diet for 15 weeks. Continuing on the diet, they were treated by daily oral gavage with vehicle, DPPC or DLPC for last 2 weeks, and glucose homeostasis was assessed with a standard glucose tolerance test. *$P<0.05$, **$P<0.01$ vs veh.

Finally, we show that effects of DLPC are LRH-1 dependent. Mice having f/f LRH-1 gene were treated with GFP containing or Cre containing adenovirus. Only mice having the LRH-1 gene showed reductions in serum glucose levels upon administration of DLPC (FIG. 9).

Other Embodiments

All patents, patent applications including U.S. Provisional Application No. 60/988,505, filed Nov. 16, 2007, and publications mentioned in this specification are herein incorporated by reference to the same extent as if each independent patent, patent application, or publication was specifically and individually indicated to be incorporated by reference.

What is claimed is:
1. A method of treating a subject having type II diabetes, said method comprising administering to said subject an effective amount of at least one phosphatidylcholine (PC) lipid having 22-24 total carbon atoms in its fatty acid tails, wherein each fatty acid tail is 10, 11, 12, or 13 carbon atoms in length.
2. The method of claim 1, wherein said subject is a human.
3. The method of claim 1, wherein said composition comprises DUPC.

4. The method of claim 1, wherein said composition comprises DLPC.

5. The method of claim 1, wherein said composition is administered orally.

6. The method of claim 1, wherein the said lipid is present in an enriched lipid composition.

* * * * *